United States Patent
Arima

(10) Patent No.: US 10,126,925 B2
(45) Date of Patent: Nov. 13, 2018

(54) IMAGING APPARATUS AND IMAGE DISPLAY CONTROL METHOD FOR IMAGING APPARATUS

(71) Applicant: CANON KABUSHIKI KAISHA, Tokyo (JP)

(72) Inventor: Keisuke Arima, Yokohama-shi (JP)

(73) Assignee: CANON KABUSHIKI KAISHA, Tokyo (JP)

(*) Notice: Subject to any disclaimer, the term of this patent is extended or adjusted under 35 U.S.C. 154(b) by 365 days.

(21) Appl. No.: 14/920,003

(22) Filed: Oct. 22, 2015

(65) Prior Publication Data
US 2016/0041731 A1    Feb. 11, 2016

Related U.S. Application Data

(63) Continuation of application No. 12/630,129, filed on Dec. 3, 2009.

(30) Foreign Application Priority Data

Dec. 25, 2008 (JP) ................. 2008-331191

(51) Int. Cl.
| | |
|---|---|
| G06F 3/048 | (2013.01) |
| G06F 3/041 | (2006.01) |
| G01N 23/04 | (2018.01) |
| G06F 3/0484 | (2013.01) |
| A61B 6/00 | (2006.01) |

(Continued)

(52) U.S. Cl.
CPC ............ *G06F 3/04842* (2013.01); *A61B 6/00* (2013.01); *A61B 6/463* (2013.01); *A61B 6/465* (2013.01); *A61B 6/467* (2013.01); *A61B 6/468* (2013.01); *A61B 6/469* (2013.01); *A61B 6/54* (2013.01); *G06F 3/0482* (2013.01);
(Continued)

(58) Field of Classification Search
CPC .. G06F 3/0481; G06F 3/0482; G06F 3/04895; G06F 3/04817; G06F 3/04842
See application file for complete search history.

(56) References Cited

U.S. PATENT DOCUMENTS

| | | | |
|---|---|---|---|
| 6,501,827 B1 | 12/2002 | Takasawa | 378/116 |
| 6,938,216 B1 | 8/2005 | Ishisaki | 715/817 |

(Continued)

FOREIGN PATENT DOCUMENTS

| | | |
|---|---|---|
| JP | H11-009580 | 1/1999 |
| JP | 2000-166908 | 6/2000 |
| JP | 2005-253641 | 9/2005 |

*Primary Examiner* — Shourjo Dasgupta
(74) *Attorney, Agent, or Firm* — Fitzpatrick, Cella, Harper & Scinto

(57) ABSTRACT

An X-ray imaging apparatus includes a touch panel monitor configured to provide an operation unit and a display unit for imaged image on the same screen. The apparatus displays a plurality of buttons corresponding to a plurality of imaging methods, and displays with a focus a first button corresponding to a first imaging method that has entered an imaging ready state. When imaging by the first imaging method is completed, the apparatus displays an imaged image on the display unit, displays the first button in a form that shows that imaging is completed, cancels the focus of the first button, and transfers the focus to a second button corresponding to a second imaging method that next enters an imaging ready state.

12 Claims, 12 Drawing Sheets

(51) Int. Cl.
 *G06F 3/0482* (2013.01)
 *G06F 3/0488* (2013.01)
 *H04N 5/232* (2006.01)
(52) U.S. Cl.
 CPC ....... *G06F 3/0488* (2013.01); *H04N 5/23293* (2013.01); *A61B 6/4028* (2013.01)

(56) References Cited

U.S. PATENT DOCUMENTS

| | | | |
|---|---|---|---|
| 2002/0031203 A1 | 3/2002 | Polichar et al. | 378/98.2 |
| 2003/0016850 A1* | 1/2003 | Kaufman | G06F 19/321 |
| | | | 382/128 |
| 2004/0068170 A1 | 4/2004 | Wang et al. | 600/407 |
| 2005/0053199 A1 | 3/2005 | Miles | 378/197 |
| 2006/0005124 A1 | 1/2006 | Speicher | 715/514 |
| 2007/0036268 A1 | 2/2007 | Matsuno | 378/98.2 |
| 2007/0150385 A1 | 6/2007 | Ode | 705/30 |
| 2009/0036268 A1 | 2/2009 | Olson | 378/98.2 |
| 2009/0054755 A1 | 2/2009 | Shibashi | 600/407 |
| 2009/0132942 A1* | 5/2009 | Santoro | G06F 3/0481 |
| | | | 715/765 |

* cited by examiner

FIG. 2

| EXAMINATION ID | PATIENT ID | PATIENT NAME | IMAGING METHOD | IMAGING |
|---|---|---|---|---|
| 200022 | 121212 | CANON TAROU | CRANIUM FRONT | NOT IMAGED |
| 200022 | 121212 | CANON TAROU | CHEST FRONT | NOT IMAGED |
| 200022 | 121212 | CANON TAROU | CHEST SIDE | NOT IMAGED |
| 200022 | 121212 | CANON TAROU | ABDOMEN FRONT | NOT IMAGED |
| 200022 | 121212 | CANON TAROU | ABDOMEN SIDE | NOT IMAGED |

FIG. 6

| EXAMINATION ID | PATIENT ID | PATIENT NAME | IMAGING METHOD | IMAGING STATUS |
|---|---|---|---|---|
| 200022 | 121212 | CANON TAROU | CRANIUM FRONT | IMAGING COMPLETED |
| 200022 | 121212 | CANON TAROU | CHEST FRONT | IMAGING COMPLETED |
| 200022 | 121212 | CANON TAROU | CHEST SIDE | NOT IMAGED |
| 200022 | 121212 | CANON TAROU | ABDOMEN FRONT | NOT IMAGED |
| 200022 | 121212 | CANON TAROU | ABDOMEN SIDE | NOT IMAGED |

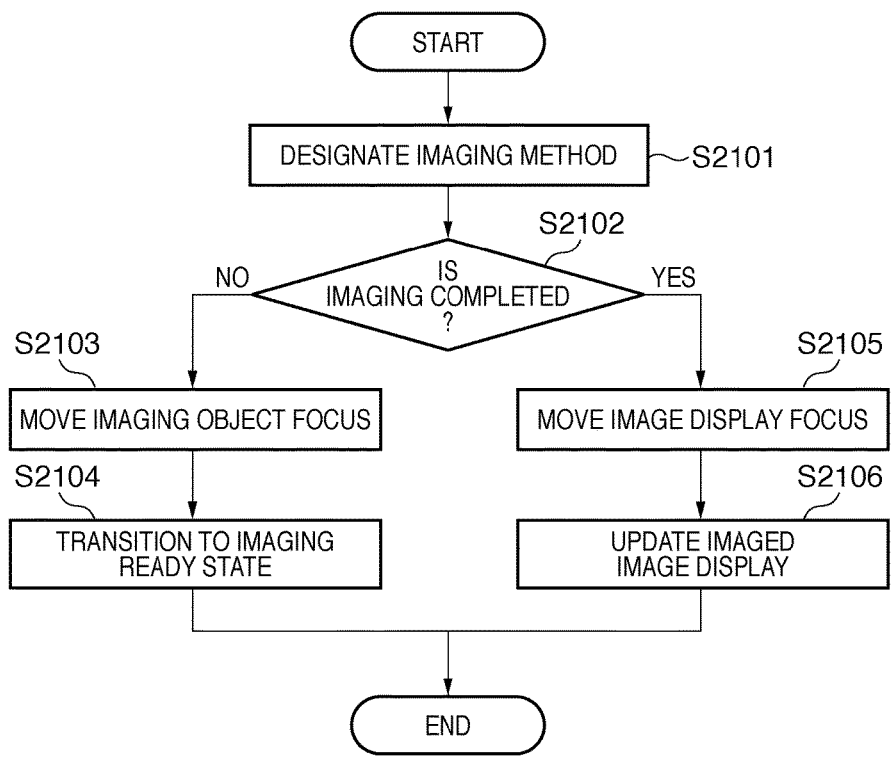

F I G. 9

| | | | Not READY | |
|---|---|---|---|---|
| EXAMINATION ID : 987654 | | | TUBE VOLTAGE : | IRRADIATION TIME : |
| NAME : CANON TAROU | GENDER : MALE | | TUBE CURRENT : | MASS VALUE : |
| PATIENT ID : 123456 | BIRTH DATE : 2008 / 06 / 26 | | | |

- 3002
- 3010
- 3006
- 3007A (CRANIUM FRONT)
- 3007B (CHEST FRONT)
- 3007C (CHEST SIDE)
- 3007D (ABDOMEN FRONT)
- 3009 (ABDOMEN SIDE)
- 3008
- 3013 (OK)

3011:
- CRANIUM FRONT
- CRANIUM SIDE
- CERVICAL VERTEBRAE FRONT
- CERVICAL VERTEBRAE SIDE
- CHEST FRONT
- CHEST SIDE
- ABDOMEN FRONT
- ABDOMEN SIDE
- PELVIS FRONT
- PELVIS SIDE
- HUMERUS FRONT
- CUBITAL JOINT
- FOREARM BONE
- HIP JOINT FRONT
- FEMUR FRONT

3012: PREVIOUS PAGE / NEXT PAGE

3001

IMAGING APPARATUS AND IMAGE DISPLAY CONTROL METHOD FOR IMAGING APPARATUS

RELATED APPLICATIONS INVENTION

This application is a continuation of application Ser. No. 12/630,129, filed Dec. 3, 2009, claims benefit of that application under 35 U.S.C. § 120, and claims benefit under 35 U.S.C. § 119 of Japanese Patent Application No. 2008-331191, filed Dec. 25, 2008. The entire contents of each of the mentioned prior applications are hereby incorporated by reference herein.

BACKGROUND OF THE INVENTION

Field of the Invention

The present invention relates to an imaging apparatus that performs imaging of images and an image display control method for an imaging apparatus.

Description of the Related Art

Conventionally, in radiographic imaging in the field of medical treatment, X-ray imaging is performed by irradiating X-rays at a subject and detecting the intensity of X-rays that are transmitted through the subject. Recently, imaging systems that convert X-rays that are transmitted through a subject into electrical signals to obtain an X-ray image as digital data are in widespread use.

An X-ray imaging system includes an X-ray generator that irradiates X-rays, an X-ray imaging apparatus that detects X-rays and forms an image, a controller that controls these apparatuses, an input unit that accepts inputs by an operator, and a display unit that displays examination information and imaged image information.

In hospitals, X-ray examinations that use the above-described X-ray imaging system are routinely performed. In general, to conduct an X-ray examination, a physician of the relevant medical care department creates an examination request form in which an imaging location and imaging method are described. At the radiology department, a radiographer operates the X-ray imaging system in accordance with the examination request form to perform the X-ray examination.

Currently, some hospitals are also equipped with an internal hospital network. Various medical devices are connected to the internal hospital network, and a hospital information system (HIS), a radiography information system (RIS), a medical image server and the like are linked together thereby.

In a hospital equipped with an internal hospital network, instead of issuing an examination request form, a physician issues an examination request for an X-ray examination at an HIS terminal. At the radiology department, the examination request that has been accepted at an RIS terminal is incorporated into the X-ray imaging system, and an X-ray examination is performed according to the examination request of the physician.

Many X-ray examinations require imaging of a plurality of images. In the case of an examination in which a large number of images are imaged, it is difficult for the radiographer to ascertain the progress of the examination with respect to where the next imaging location is and to how many images have currently been completed. If the situation reaches a stage where the radiographer is unable to ascertain the progress of the examination, the radiographer must develop the imaged images on X-ray film and confirm the situation.

Regarding this problem, a method has been proposed that displays a list of requested imaging items on a display monitor so that the progress of an examination can be checked with a single glance (for example, see Japanese Patent No. 3259659). According to this method, the display form is one that allows a radiographer to easily determine which imaging item is the current object, and whether imaging has not yet been performed or has been completed for each imaging item. Hence, it is extremely easy for a radiographer to ascertain the examination progress.

When a radiographer performs an X-ray examination, first the radiographer inputs patient information such as a patient ID and a patient name, and also inputs imaging information that pre-programs a plurality of imaging methods. Thereafter, the radiographer starts the examination.

In a case where an imaging request is received by means of an RIS terminal, a patient to be examined is selected from a patient list, and the examination is started. In this case, imaging information is also attached to the patient information, and is input simultaneously with selection of the patient. Next, the radiographer selects an item for imaging from a list of imaging methods that has been input, and starts X-ray irradiation. The imaged image is immediately displayed on a liquid crystal monitor, and if imaging has been appropriately performed the radiographer moves to the next imaging. When all imaging is completed, the radiographer ends the examination, and moves on to perform imaging of the next patient.

In this kind of examination flow, the radiographer performs an examination while operating several types of windows. First, the radiographer inputs examination information using a patient information input window through which patient information is input and a program input window through which an imaging program is input, and starts the examination. After starting the examination, the radiographer sets imaging conditions and checks imaged images using an imaging condition setting window that sets imaging conditions, and an imaged image display window that displays imaged images. Further, when image processing is necessary, the radiographer operates an image processing window.

Naturally, when transitioning between windows, an operation is necessary to make the windows transition. For example, according to the conventional X-ray imaging system, when X-ray imaging is performed, the imaged images are displayed on the imaged image display window, and after checking that imaging has been performed appropriately, the radiographer pushes a button that confirms the image is appropriate, and thereby causes the window to transition to the next imaging condition setting window. Accordingly, each time an X-ray image is imaged, it is necessary for the radiographer to perform an image confirmation operation.

However, at a facility in which X-ray examinations are performed with a high degree of urgency such as at a medical emergency center, it is necessary to perform required imaging in as short a time period as possible and then move to lifesaving treatment. According to the workflow described above it is necessary to temporarily leave the patient's side and confirm an image each time imaging is performed. Therefore, an extremely large amount of time is lost by that workflow.

Thus, the present inventors considered that imaging of multiple images can be performed swiftly by providing an imaging condition setting window and an imaged image display window on one screen, and omitting the labor of image confirmation. In order to omit an operation to confirm images, it is necessary to transition to a state in which imaging in the next imaging method is possible, and to also place the apparatus on standby for X-ray irradiation, even when on standby for an image processing operation for an imaged image. However, there is the problem that it is necessary to control two focuses in an imaging method list. The two focuses are the imaging method of the imaged image that is being displayed and the imaging method that is in an imaging ready state.

SUMMARY OF THE INVENTION

The present invention has been made in consideration of the above described problems, and provides an imaging apparatus and an image display control method that appropriately control a plurality of focuses in accordance with attributes of imaging methods, and realize an efficient imaging workflow in which the state of progress of an examination is easily ascertained.

According to one aspect of the present invention, there is provided an imaging apparatus capable of imaging a subject using a plurality of imaging methods that are previously programmed, comprising: a touch panel monitor configured to provide an operation unit relating to imaging and a display unit for images obtained by imaging on the same screen; and a display control unit configured to control a display on the touch panel monitor; wherein the display control unit: displays a plurality of buttons corresponding to the plurality of imaging methods, respectively, on the operation unit in a previously programmed order; displays a first button corresponding to a first imaging method that has entered an imaging ready state among the plurality of buttons in a focused state by means of an imaging ready focus that indicates an imaging ready state; and when imaging by the first imaging method is completed, displays an image obtained by the relevant imaging on the display unit and cancels the imaging ready focus of the first button, and next causes the imaging ready focus to transition to a second button corresponding to a second imaging method that enters an imaging ready state and also displays the first button in a focused state by means of an image display focus that indicates that an image obtained by imaging by the first imaging method is being displayed on the display unit.

Further features of the present invention will become apparent from the following description of exemplary embodiments with reference to the attached drawings.

BRIEF DESCRIPTION OF THE DRAWINGS

FIG. 2 is a view that illustrates an examination information management table according to an embodiment of the present invention.

FIG. 6 is a view that illustrates an examination information management table according to an embodiment of the present invention.

FIG. 8 is a flowchart that represents focus control processing when designating an imaging method according to an embodiment of the present invention.

FIG. 9 is a view that illustrates a program editing window display example according to an embodiment of the present invention.

DESCRIPTION OF THE EMBODIMENTS

Various exemplary embodiments, features, and aspects of the present invention will be described in detail below with reference to the drawings.

Figure 1:
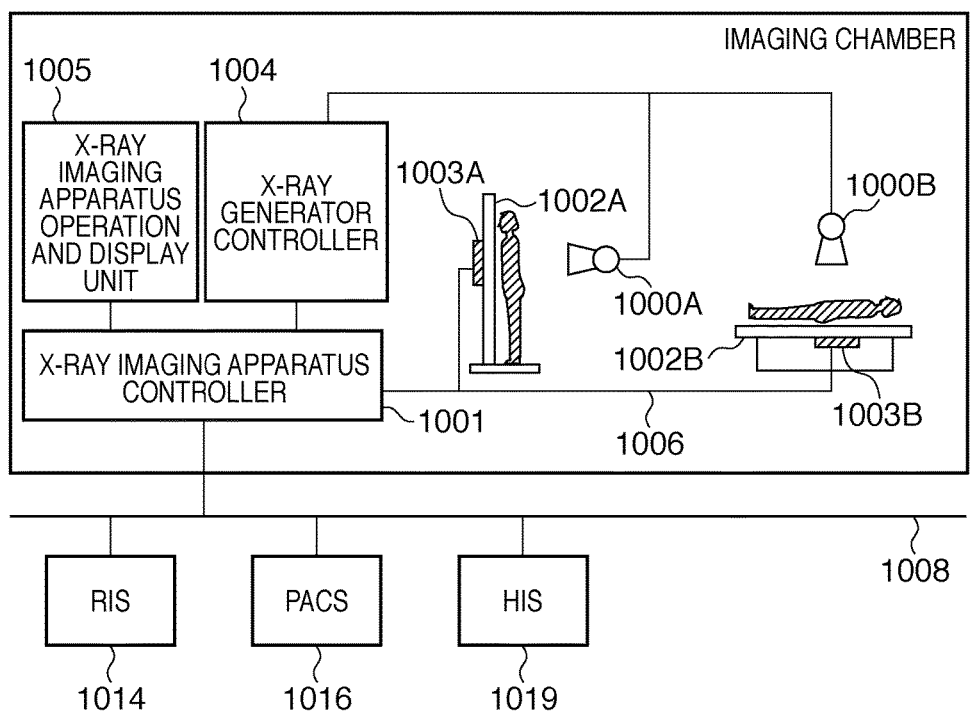
FIG. 1 is a view that illustrates an outline configuration of an X-ray imaging system according to an embodiment of the present invention.

FIG. 1 is a view that illustrates the configuration of an X-ray imaging system according to the present embodiment.

The X-ray imaging apparatus includes an imaging controller 1001, an operation and display unit 1005, X-ray tubes 1000A and 1000B that are X-ray generators, and an X-ray tube controller 1004 that controls the X-ray tubes. The operation and display unit 1005 is configured by a touch panel monitor that provides an operation unit relating to imaging and a display unit of images obtained by imaging on the same screen. The touch panel monitor and an unshown keyboard accept input operations from a technician.

X-ray imaging units 1003A and 1003B are connected to the imaging controller 1001 via a data cable 1006 used for a power supply, image transfer, and control signals. The X-ray imaging units 1003A and 1003B are installed on imaging platforms 1002A and 1002B that are arranged in a standing position and a lying position, respectively.

The imaging controller 1001 can be configured with a typical computer device that has an unshown CPU, ROM, RAM, hard disk and the like. The imaging controller 1001 is connected via a network 1008 with a radiology department internal information system (RIS) 1014, an image server (PACS) 1016, and a hospital internal information system (HIS) 1019. The imaging controller 1001 receives examination information from the RIS 1014 and holds the examination information. The imaging controller 1001 controls the X-ray imaging units 1003A and 1003B and the X-ray tube controller 1004 according to inputs by an operator. The imaging controller 1001 also functions as a display control unit with respect to the touch panel monitor that comprises the operation and display unit 1005.

A technician (operator) inputs examination information in accordance with an examination request from the RIS 1014. Specifically, input of examination information includes input of patient information including a patient name and a patient ID, and input of imaging information in which a plurality of imaging methods are previously programmed. When input of examination information is completed and the operator presses an examination start button, the input of examination information is confirmed. The confirmed examination information is stored in a memory such as an unshown RAM inside the imaging controller 1001 as an examination information management table as shown in FIG. 2. Initially, "not imaged" is set as the imaging status for all imaging methods.

Figure 3:
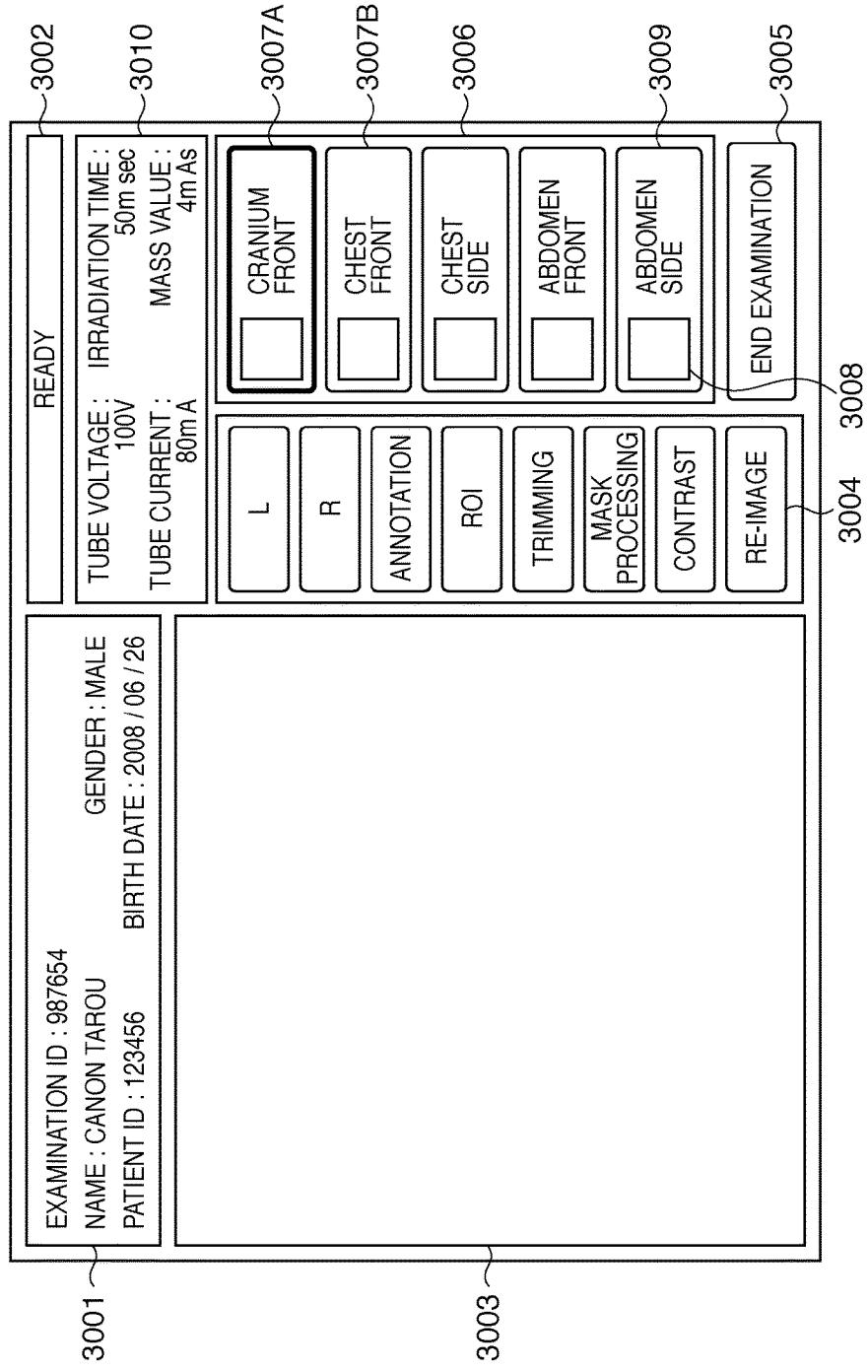
FIG. 3 is a view that illustrates an imaging window display example according to an embodiment of the present invention.

An imaging window as shown in FIG. 3 is displayed on the operation and display unit 1005 of the imaging apparatus. Examination information such as an examination ID, a patient ID, and a patient name are displayed in an examination information display region 3001. The status of the X-ray imaging apparatus, such as an X-ray irradiation ready state, and an error message and the like are displayed in a message region 3002. Further, an image obtained by imaging is displayed in an imaged image display region 3003. An image processing setting region 3004 is an operation unit for performing image processing such as attachment of a lead mark or annotation, ROI adjustment, or trimming on an image in the imaged image display region 3003.

Imaging method buttons 3007 corresponding to respective imaging methods are lined up in the imaging method list 3006 in a previously programmed order in accordance with imaging information that has been input. Imaging method names 3009 are displayed on imaging method buttons 3007A and 3007B and the like. The imaging method buttons 3007A and 3007B and the like also include a thumbnail region 3008 that displays a thumbnail image of an imaged image.

Upon transitioning to the imaging window, a button (first button) corresponding to an imaging method (first imaging method) that is in an imaging ready state and for which the imaging status is "not imaged" automatically enters a selected state as shown by a cranium front button 3007A in FIG. 3. A focus (hereinafter, referred to as "imaging object focus") that indicates that the cranium front button 3007A that enters a selected state is the next imaging object is assigned to the cranium front button 3007A.

Accompanying the transition of the imaging object focus, imaging conditions that have been set with respect to the front cranium are displayed in an imaging condition setting region 3010, and information such as a tube voltage, a tube current, and an irradiation time are sent to the X-ray tube controller 1004. When preparations are in order for the X-ray tube controller 1004 and the X-ray imaging unit 1003 that is to be used for imaging, the X-ray imaging apparatus transitions to an imaging ready state and a message ("READY") indicating that the X-ray imaging apparatus is in an imaging ready state is displayed in the message region 3002.

Figure 4:
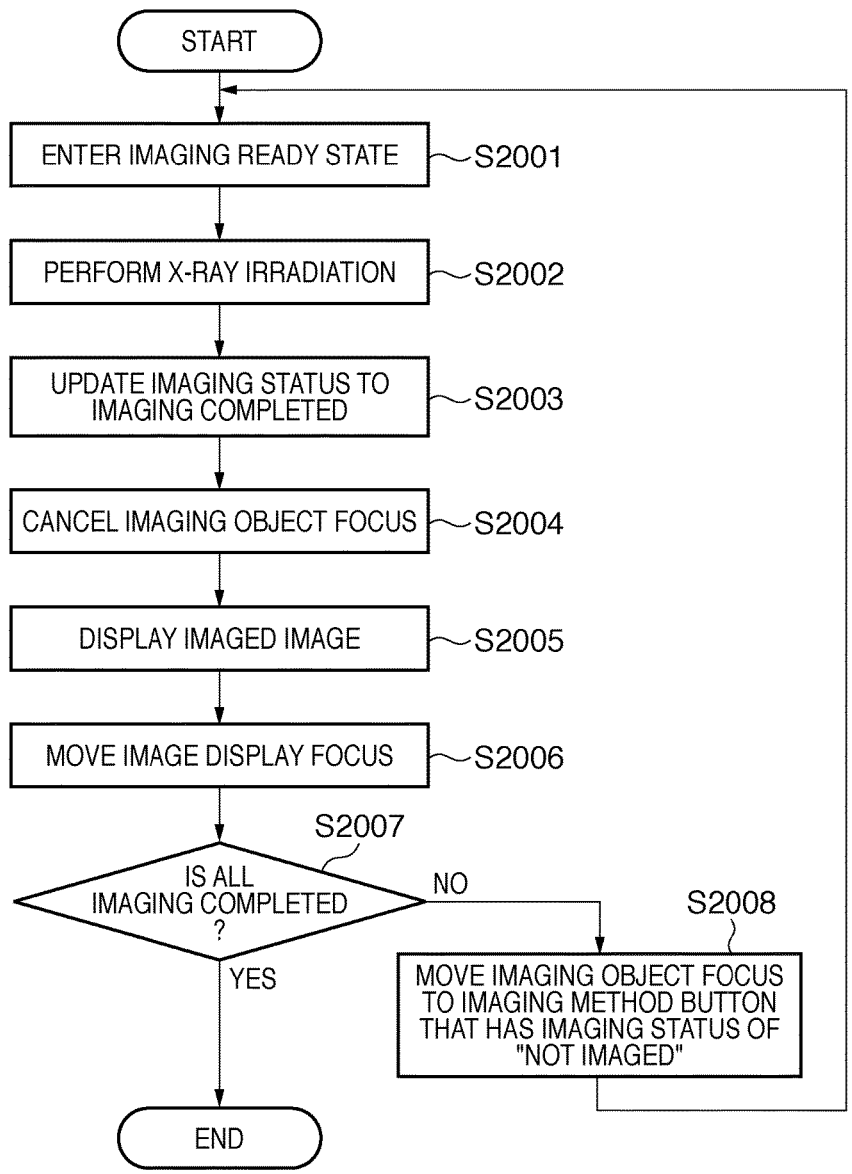
FIG. 4 is a flowchart that represents focus control processing at a time of X-ray imaging according to an embodiment of the present invention.

FIG. 4 is a view that represents the flow of focus control processing at a time of X-ray imaging according to the present embodiment. The operator confirms the imaging method and performs settings for imaging and positioning of the patient. When the imaging preparations have been completed, the X-ray imaging apparatus enters an imaging ready state (step S2001). When the operator presses an X-ray irradiation switch an X-ray image is imaged (step S2002). When X-ray irradiation is completed, the imaging status corresponding to the cranium front button 3007A in the examination information management table is updated to "imaging completed" (step S2003), and the imaging object focus is cancelled (step S2004).

The imaging controller 1001 takes in image data from the X-ray imaging unit 1003. The image data is subjected to image processing according to image processing conditions that are set for the imaging method, and is then displayed on the imaged image display region 3003 (step S2005). Accompanying the display of the imaged image, a focus (hereinafter, referred to as "image display focus") that indicates the imaging method of the displayed image is assigned to the cranium front button 3007A (step S2006). Simultaneously, as a form that shows that imaging by the imaging method in question is completed, a thumbnail image is also displayed in a thumbnail region 3008 inside the imaging method button. Thereby, the operator can distinguish at a glance whether the imaging status thereof is "not imaged" or "imaging completed".

The imaging object focus moves to a chest front button 3007B (second button) for which the imaging status is "not imaged" (step S2008). Thereafter, the X-ray imaging apparatus transitions to the next imaging ready state with respect to the imaging method (second imaging method) at the transition destination (step S2001).

As described above, two focuses that are in accordance with a value for the imaging status are present in the imaging window, and the imaging controller 1001 performs focus control so as to independently operate each focus.

Figure 5:
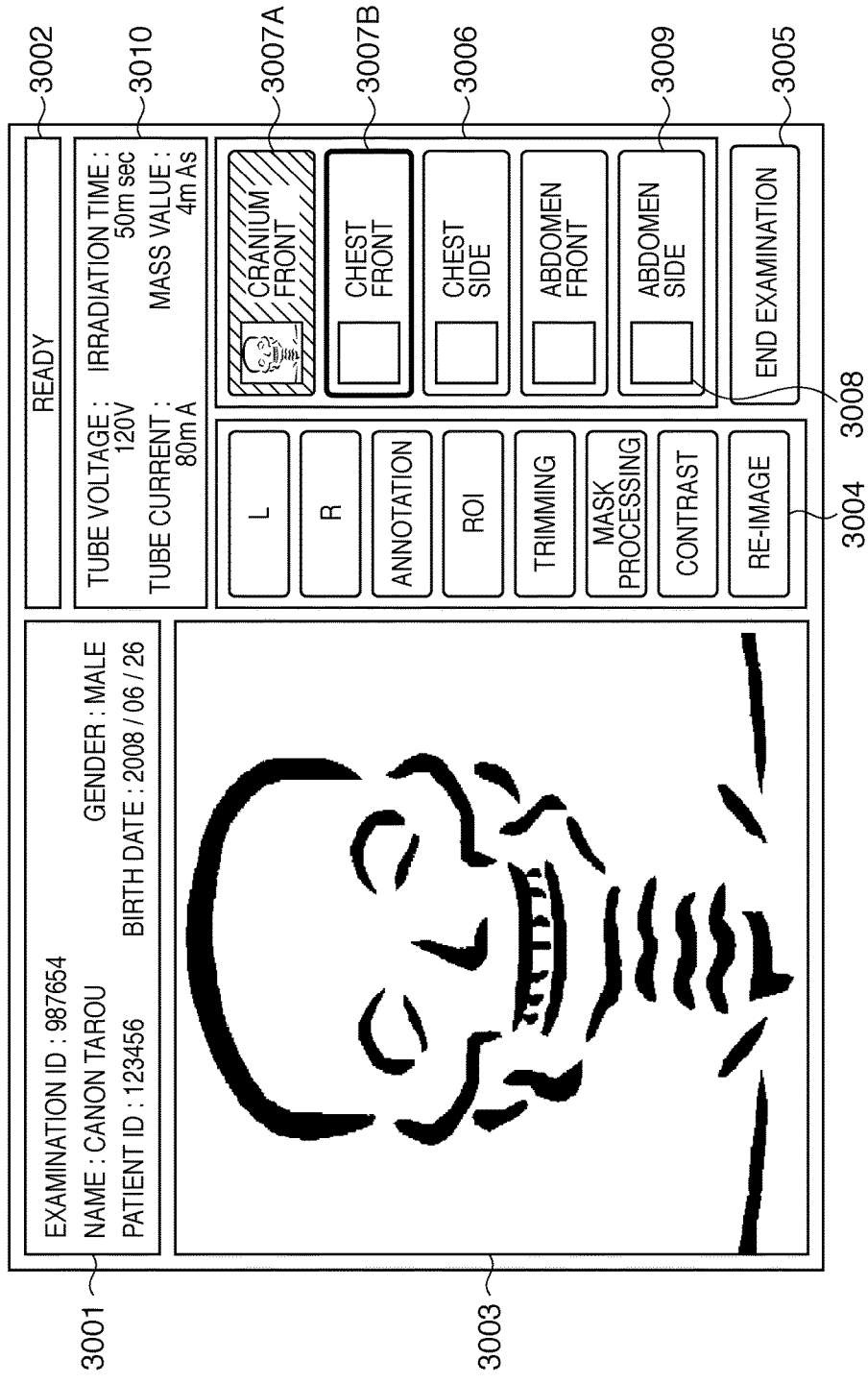
FIG. 5 is a view that illustrates an imaging window display example according to an embodiment of the present invention.

After execution of focus automatic transition processing, the imaging window enters a state as shown, for example, in FIG. 5, in which two focuses for an imaging object and an image display, respectively, are present in the imaging method list 3006. In the message region 3002, an imaging ready state is displayed with respect to the chest front button 3007B that has the imaging object focus, and the X-ray irradiation switch can be pressed if imaging is possible. Meanwhile, image processing buttons such as "Lead Mark", "Annotation", "ROI Adjustment", and "Trimming" are displayed in the image processing setting region 3004, and processing can be performed with respect to the image that has been imaged using the cranium front button 3007A that has the image display focus. Accordingly, operations are possible with respect to the two imaging method buttons that have the imaging object focus and the image display focus, respectively.

Figure 7:
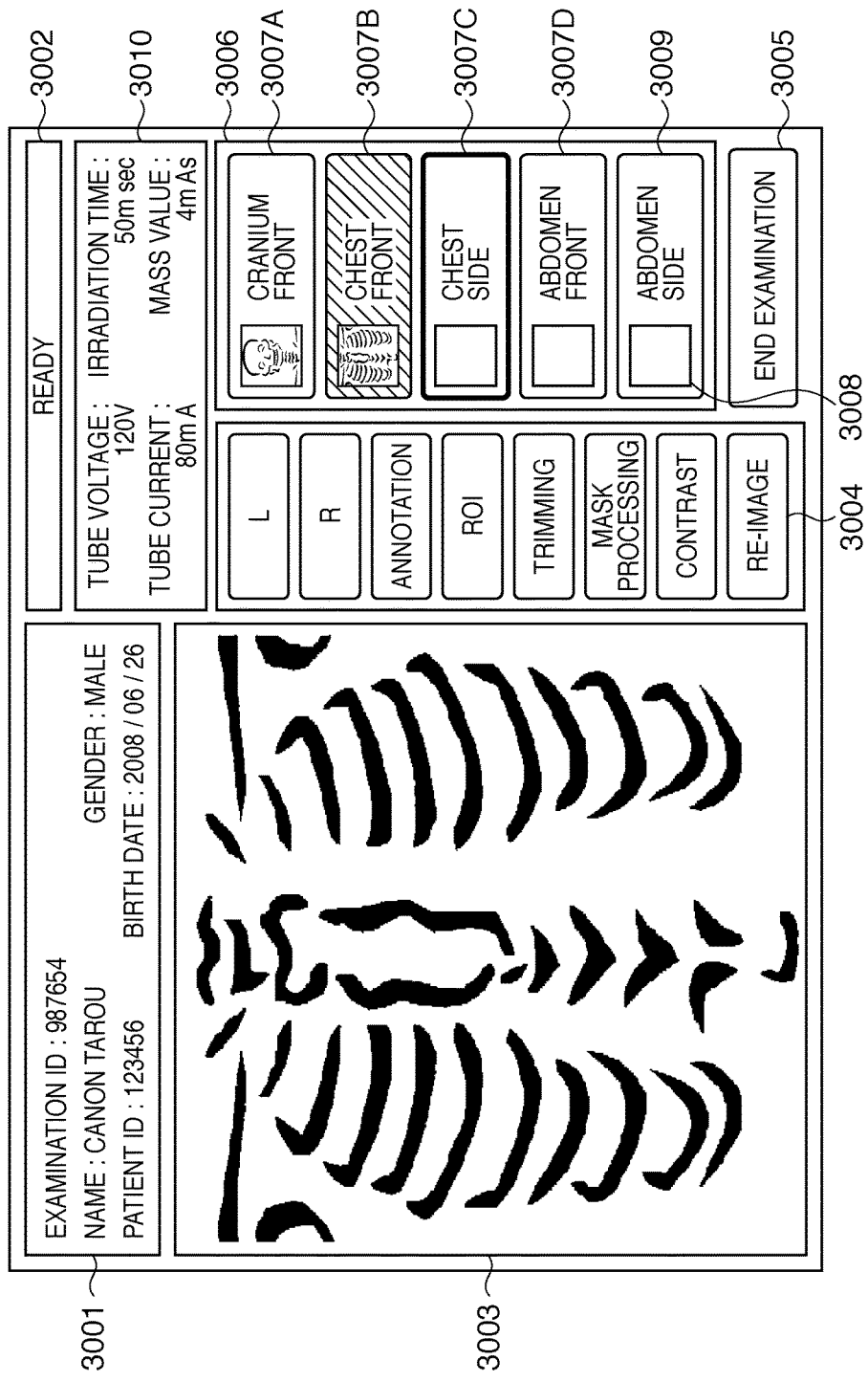
FIG. 7 is a view that illustrates an imaging window display example according to an embodiment of the present invention.

When the operator proceeds with imaging again with the same focus control, the examination information management table is updated as shown in FIG. 6, and the window appears as shown in FIG. 7. Although according to the aforementioned focus control the imaging is performed in order from the top button of the imaging method buttons 3007 that are lined up in the imaging method list 3006, the order of an examination request may not be an order appropriate for imaging.

For example, according to the present embodiment, imaging is programmed so as to be performed in the order of chest front, chest side, and abdomen front. However, by imaging the abdomen front next after the chest front is imaged, imaging can be performed by only altering the settings of the X-ray imaging unit 1003, and without having to adjust the position of the patient. When the number of times that the position of a patient is adjusted during a series of examinations is kept as low as possible, as in this example, imaging can be performed without burdening the patient.

In a case in which the imaging order is not appropriate as described above, the operator designates the imaging method buttons, and designates the next imaging object by means of the imaging method buttons 3007. The behavior for designating an imaging method will now be described using the flowchart of focus control that accompanies designation of an imaging method that is shown in FIG. 8.

When the abdomen front button 3007D is pressed in the state shown in FIG. 7 (step S2101), the imaging controller 1001 refers to the imaging status from the examination information management table (step S2102). Since the imaging status of the abdomen front button 3007D is "not imaged", the front abdomen is designated as the next imaging object. The imaging controller 1001 moves the imaging object focus from the chest side button 3007C (step S2103), and causes the X-ray imaging apparatus to transition to an imaging ready state (step S2104).

When the cranium front button 3007A has been pressed, since the imaging status is "imaging completed" the imaging controller 1001 determines that the cranium front has been designated as an image display object, and moves the image display focus from the chest front button 3007B (step S2105). Simultaneously, the imaging controller 1001 displays an image of the front cranium in the image display region (step S2106).

Figure 10:
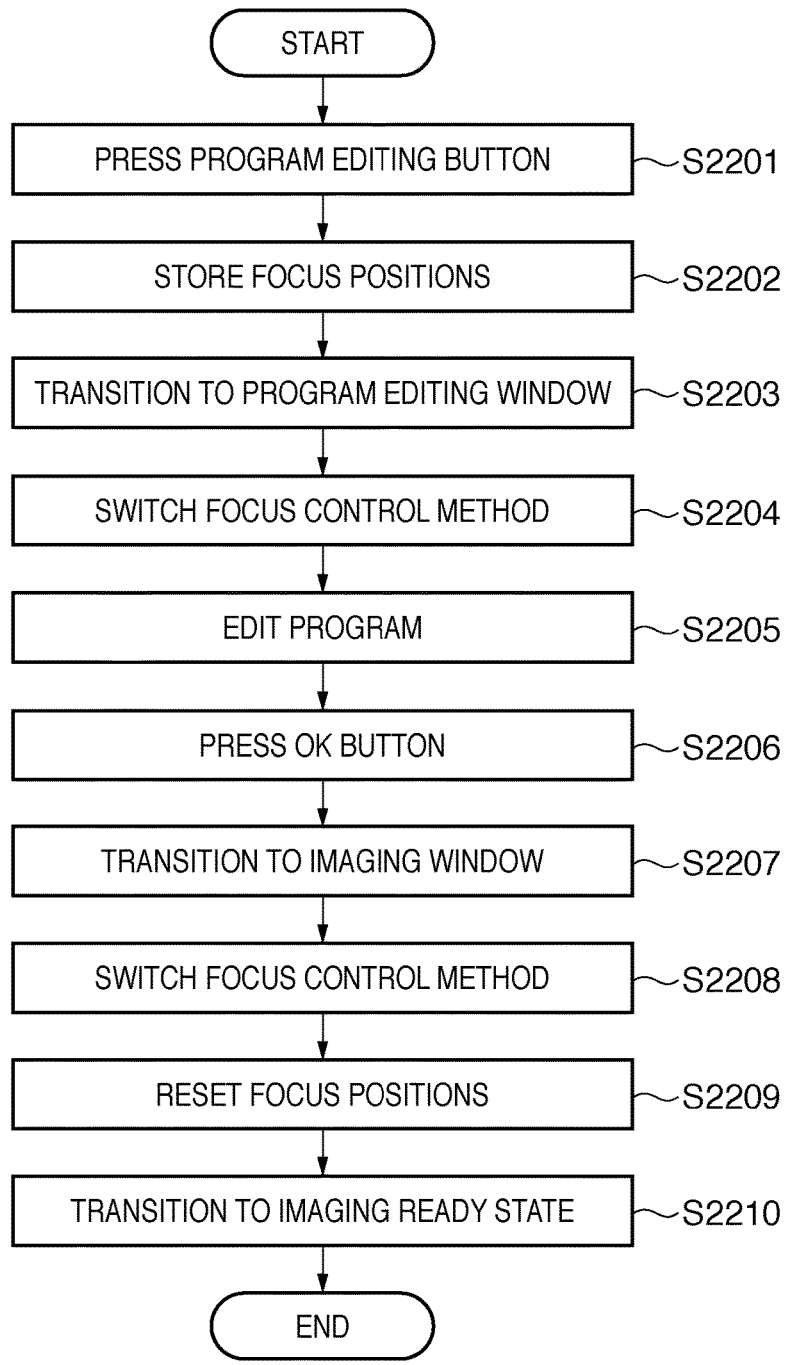
FIG. 10 is a flowchart that represents focus control processing at a time of a window transition according to an embodiment of the present invention.

There are also cases in which an operator edits the imaging program and performs additional imaging in the course of an examination. FIG. 9 illustrates an example of a program editing window. FIG. 10 illustrates a flowchart in the case of performing program editing.

When the program editing button 3099 is pressed (step S2201), the imaging controller 1001 stores the respective positions of the imaging object focus and the image display focus (step S2202). Thereafter, the imaging controller 1001 transitions to the program editing window (step S2203). In the imaging method list 3006 of the program editing window, the focus control method switches to a single focus control that is unrelated to the imaging status (step S2204).

In the program editing window, imaging method addition buttons 3011 are lined up for adding imaging method buttons to the imaging method list 3006. When an imaging method addition button is pressed, an imaging method button is newly inserted after the imaging method button 3007B to which the focus is assigned (step S2205).

When addition of imaging method buttons is finished, the operator confirms the editing by pressing an OK button 3013 (step S2206). The display then returns to the imaging window (step S2207). The focus control method switches to multi-focus control for each imaging status (step S2208). At this time, the imaging object focus and image display focus are reset to the appropriate imaging method buttons according to the settings stored when transitioning to the program editing window (step S2209). By storing the focus positions and then resetting those positions, it is possible to return the X-ray imaging apparatus to the state immediately prior to transitioning to the program editing window, and thus avoid confusion for the operator (step S2210). In this way, it is possible to add, alter, or delete a plurality of imaging methods.

Figure 11:
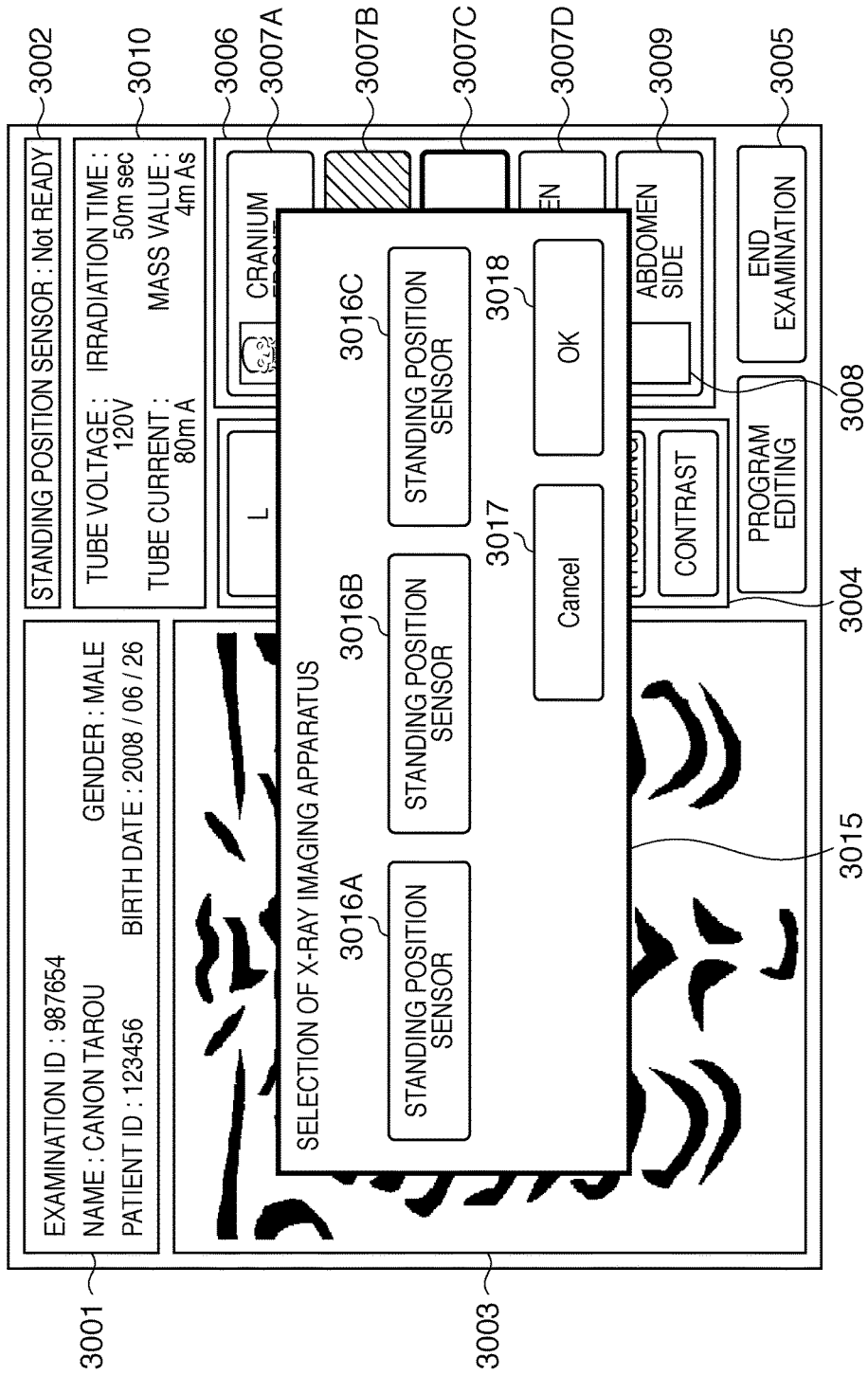
FIG. 11 is a view that illustrates an X-ray imaging apparatus changing window display example according to an embodiment of the present invention.

Information that specifies an X-ray imaging apparatus to be used for imaging is associated with the imaging methods, and information of the X-ray imaging apparatus that has entered an imaging ready state is displayed in the message region 3002. For example, in the case of the X-ray imaging apparatus shown in FIG. 7 the X-ray imaging unit 1003A that is in a standing position has transitioned to an imaging ready state. However, in this case it is assumed that the subject has a physical disability and it is difficult for the subject to maintain a standing posture. In this case, imaging is performed using the X-ray imaging unit 1003B that is in a lying position and does not require the subject to stand upright. According to the window of the present embodiment, when the imaging method that has the imaging object focus is pressed again, a window for changing the X-ray imaging apparatus is displayed. FIG. 11 illustrates an example of an X-ray imaging apparatus changing window. The operator can select an X-ray imaging apparatus to be used for imaging by pressing one of X-ray imaging apparatus buttons 3016A, 3016B, and 3016C. When the operator presses an OK button 3018, the X-ray imaging apparatus changing window closes, and the X-ray imaging apparatus transitions to an imaging ready state at the X-ray imaging apparatus which has been selected by the operator. If a Cancel button 3017 is pressed, the state returns to an imaging ready state at the original X-ray imaging apparatus.

Figure 12:
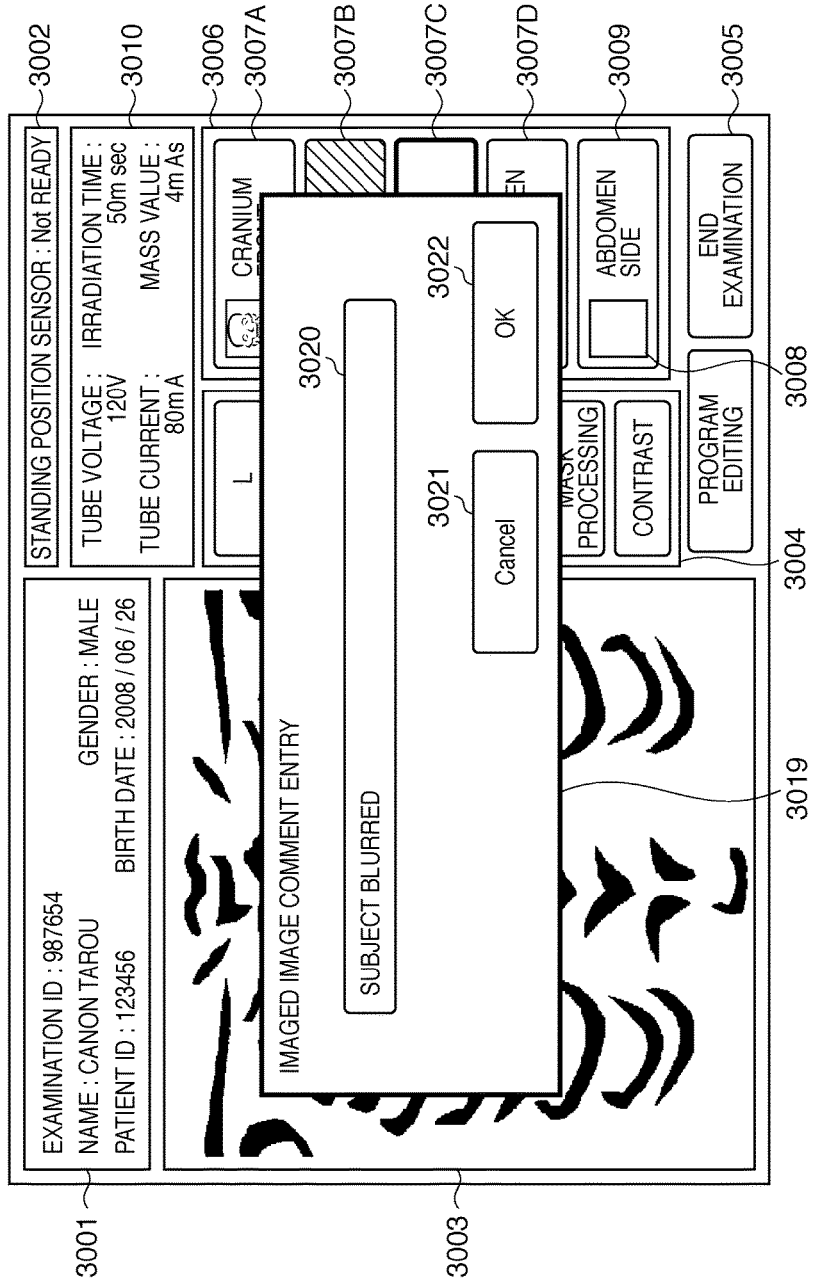
FIG. 12 is a view that illustrates an associated information editing window display example according to an embodiment of the present invention.

In some cases, the operator leaves a comment relating to an imaged image after imaging for a reason such as an imaging mistake or to give an opinion. When the imaging method that has the image display focus is pressed again on the window of the present embodiment, a window is displayed for editing information associated with the image that is being displayed. FIG. 12 illustrates an example of an associated information editing window. The operator can enter a comment regarding the imaged image into an associated information entry field 3020. Subsequently, when the operator presses an OK button 3022, the associated information editing window closes and the comment that is entered is stored as associated information of the imaging method. In this connection, when a Cancel button 3021 is pressed, the associated information editing window closes without storing associated information.

As described above, when an imaging method is re-designated by pressing once more an imaging method button that is in a selected state, the imaging controller 1001 controls the window so as to perform a different operation in accordance with the imaging status.

According to the present embodiment, an example has been used in which a connection is made to the network 1008 and the RIS 1014 is used to acquire information of an examination to be carried out. However, the present invention can also be applied to a plurality of imaging methods that are registered on an X-ray imaging apparatus, using operations that do not connect to the network 1008.

Further, although according to the present embodiment an example is used of switching between multi-focus control and single-focus control in accordance with an imaging status, the present invention can also be applied to a case of switching between a plurality of multi-focus controls.

According to the present invention, by mixing imaging methods that have different imaging statuses inside an imaging method list and adopting a display such that the imaging statuses can be confirmed at one glance, an imaging apparatus can be realized with which the state of progress of an examination is easy to ascertain. Further, according to the present invention, since operations are enabled with respect to imaging methods for both the next imaging object and also an image display object, an efficient imaging workflow that requires a small number of operations can be realized.

OTHER EMBODIMENTS

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An imaging apparatus comprising:
   a storage unit configured to store a plurality of imaging methods;
   a memory storing a program; and
   one or more processors which, by executing the program, function as:
   a display control unit configured to display a plurality of imaging buttons each corresponding to the plurality of imaging methods on a screen, and to display an image obtained by imaging on the screen, the imaging buttons being lined up in an imaging method list;
   a selection unit configured to select one of the displayed plurality of buttons; and
   an imaging unit configured to perform imaging by an imaging method corresponding to the selected button read from the storage unit, wherein
   the plurality of buttons include a first button that indicates that imaging by a first imaging method is in a ready state; a second button that indicates that an image obtained by imaging by a second imaging method is being displayed on the screen; a third button that indicates that imaging by a third imaging method is completed, and an image obtained by imaging by the third imaging method is not displayed on the screen; and a fourth button that indicates that imaging by a fourth imaging method has commenced but is not completed,
   the display control unit displays the first button, the second button, and the third button on the screen in different display format, and displays the fourth button in the same display format as the third button, and
   when an imaging method is completed, a focus of the imaging button corresponding to the imaging method automatically transitions to a next button of the imaging button in the imaging method list and the imaging apparatus transitions to an imaging ready state.

2. The apparatus according to claim 1, wherein the display control unit displays a thumbnail image of the image obtained by imaging by the second imaging method on the second button.

3. The apparatus according to claim 1, wherein the display control unit displays a message indicating that imaging by the first imaging method is in a ready state, after imaging by the second imaging method.

4. The apparatus according to claim 1, wherein the display control unit displays at least one image processing button for designating image processing for the image obtained by imaging by the second imaging method and displayed on the screen.

5. The apparatus according to claim 1, wherein the display control unit displays the image obtained by imaging by the third imaging method on the screen in response to selection of the third button.

6. The apparatus according to claim 1, further comprising a unit configured to perform addition, alteration, or deletion of the plurality of imaging methods.

7. The apparatus according to claim 1, wherein the screen comprises a touch-sensitive screen.

8. An imaging apparatus comprising:
   a storage unit configured to store a plurality of imaging methods;
   a memory storing a program; and
   one or more processors which, by executing the program, function as:
   a display control unit configured to display a plurality of imaging buttons each corresponding to the plurality of imaging methods on a screen and to display an image obtained by imaging on the screen, the imaging buttons being lined up in an imaging method list;
   a selection unit configured to select one of the displayed plurality of buttons; and
   an imaging unit configured to perform imaging by an imaging method corresponding to the selected button read from the storage unit, wherein
   the plurality of buttons include a first button that indicates that imaging by a first imaging method is in a ready state; a second button that indicates that an image obtained by imaging by a second imaging method is being displayed on the screen; a third button that indicates that imaging by a third imaging method is completed, and an image obtained by imaging by the third imaging method is ready to be displayed on the screen; and a fourth button that indicates that imaging by a fourth imaging method has commenced but is not completed,
   the display control unit displays the first button, the second button, and the third button on the screen in different display format, and displays the fourth button in the same display format as the third button, in order to realize an efficient imaging workflow in which the state of progress of an examination is easily ascertained, and
   when an imaging method is completed, a focus of the imaging button corresponding to the imaging method automatically transitions to a next button of the imaging button in the imaging method list and the imaging apparatus transitions to an imaging ready state.

9. A method for controlling displaying of an image executed by an imaging apparatus, the method comprising:
   displaying a plurality of imaging buttons each corresponding to a plurality of imaging methods on a screen, the imaging buttons being lined up in an imaging method list;
   selecting one of the displayed plurality of buttons; and
   performing imaging by an imaging method corresponding to the selected button, wherein
   the plurality of buttons include a first button that indicates that imaging by a first imaging method is in a ready state; a second button that indicates that an image obtained by imaging by a second imaging method is being displayed on the screen; a third button that indicates that imaging by a third imaging method is completed, and an image obtained by imaging by the third imaging method is not displayed on the screen; and a fourth button that indicates that imaging by a fourth imaging method has commenced but is not completed,
   the first button, the second button, and the third button are displayed on the screen in different display format, the fourth button is displayed on the screen in the same display format as the third button, and
   when an imaging method is completed, a focus of the imaging button corresponding to the imaging method automatically transitions to a next button of the imaging button in the imaging method list and the imaging apparatus transitions to an imaging ready state.

10. A method for controlling displaying of an image executed by an imaging apparatus, the method comprising:

displaying a plurality of imaging buttons each corresponding to a plurality of imaging methods on a screen, the imaging buttons being lined up in an imaging method list;
selecting one of the displayed plurality of buttons; and
performing imaging by an imaging method corresponding to the selected button, wherein
the plurality of buttons include a first button that indicates that imaging by a first imaging method is in a ready state; a second button that indicates that an image obtained by imaging by a second imaging method is being displayed on the screen; a third button that indicates that imaging by a third imaging method is completed, and an image obtained by imaging by the third imaging method is ready to be displayed on the screen; and a fourth button that indicates that imaging by a fourth imaging method has commenced but is not completed,
the first button, the second button, and the third button are displayed on the screen in different display format, and the fourth button is displayed on the screen in the same display format as the third button, and
when an imaging method is completed, a focus of the imaging button corresponding to the imaging method automatically transitions to a next button of the imaging button in the imaging method list and the imaging apparatus transitions to an imaging ready state.

11. A non-transitory computer-readable medium storing a program for controlling an imaging apparatus including a computer executing the program, the program comprising code for performing:
displaying a plurality of imaging buttons each corresponding to a plurality of imaging methods on a screen, the imaging buttons being lined up in an imaging method list;
selecting one of the displayed plurality of buttons; and
performing imaging by an imaging method corresponding to the selected button, wherein
the plurality of buttons include a first button that indicates that imaging by a first imaging method is in a ready state; a second button that indicates that an image obtained by imaging by a second imaging method is being displayed on the screen; a third button that indicates that imaging by a third imaging method is completed, and an image obtained by imaging by the third imaging method is not displayed on the screen; and a fourth button that indicates that imaging by a fourth imaging method has commenced but is not completed,
the first button, the second button, and the third button are displayed on the screen in different display format, the fourth button is displayed on the screen in the same display format as the third button, and
when an imaging method is completed, a focus of the imaging button corresponding to the imaging method automatically transitions to a next button of the imaging button in the imaging method list and the imaging apparatus transitions to an imaging ready state.

12. A non-transitory computer-readable medium storing a program for controlling an imaging apparatus including a computer executing the program, the program comprising code for performing:
displaying a plurality of imaging buttons each corresponding to a plurality of imaging methods on a screen, the imaging buttons being lined up in an imaging method list;
selecting one of the displayed plurality of buttons; and
performing imaging by an imaging method corresponding to the selected button, wherein
the plurality of buttons include a first button that indicates that imaging by a first imaging method is in a ready state; a second button that indicates that an image obtained by imaging by a second imaging method is being displayed on the screen; a third button that indicates that although imaging by a third imaging method is completed, and an image obtained by imaging by the third imaging method is ready to be displayed on the screen; and a fourth button that indicates that imaging by a fourth imaging method has commenced but is not completed,
the first button, the second button, and the third button are displayed on the screen in different display format, the fourth button is displayed on the screen in the same display format as the third button, and
when an imaging method is completed, a focus of the imaging button corresponding to the imaging method automatically transitions to a next button of the imaging button in the imaging method list and the imaging apparatus transitions to an imaging ready state.

* * * * *